United States Patent
Sagawa

(10) Patent No.: US 11,633,165 B2
(45) Date of Patent: Apr. 25, 2023

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Masafumi Sagawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 352 days.

(21) Appl. No.: 16/987,393

(22) Filed: Aug. 6, 2020

(65) Prior Publication Data

US 2020/0359984 A1 Nov. 19, 2020

Related U.S. Application Data

(63) Continuation of application No. PCT/JP2018/047651, filed on Dec. 25, 2018.

(30) Foreign Application Priority Data

Mar. 9, 2018 (JP) .............................. JP2018-043231

(51) Int. Cl.
*A61B 6/00* (2006.01)
*G06T 7/55* (2017.01)
(Continued)

(52) U.S. Cl.
CPC ............ *A61B 6/5223* (2013.01); *A61B 6/466* (2013.01); *A61B 6/5235* (2013.01);
(Continued)

(58) Field of Classification Search
None
See application file for complete search history.

(56) References Cited

U.S. PATENT DOCUMENTS

| 9,093,799 B2 | 7/2015 | Kiribayashi |
| 2003/0185426 A1* | 10/2003 | Ohishi ................ A61B 8/5238 |
| | | 382/128 |

(Continued)

FOREIGN PATENT DOCUMENTS

| JP | H11190776 | 7/1999 |
| JP | 2000051214 | 2/2000 |

(Continued)

OTHER PUBLICATIONS

JPH11190776A Display for inside and contour of body, English machine translation Dec. 26, 1997 (Year: 1997).*

(Continued)

*Primary Examiner* — Nancy Bitar
(74) *Attorney, Agent, or Firm* — JCIPRNET

(57) ABSTRACT

A two-dimensional image acquisition unit acquires a plurality of two-dimensional images generated from a three-dimensional image of a patient in a case where an observation target is viewed from a plurality of different viewpoints, and a surface data acquisition unit acquires surface data of each of a plurality of structures on the patient from the three-dimensional image. A composite image generation unit generates a composite image in which a composite target image generated from the surface data and the two-dimensional image are composed, and a display switching control unit receives an operation of displaying or non-displaying any of the structures and performs display by switching between the composite image of the composite target image and the two-dimensional image corresponding to the structure to be displayed and the two-dimensional image of the structure to be non-displayed.

10 Claims, 13 Drawing Sheets

(51) Int. Cl.
G06T 7/00 (2017.01)
G06T 15/08 (2011.01)

(52) U.S. Cl.
CPC .............. G06T 7/0012 (2013.01); G06T 7/55 (2017.01); G06T 15/08 (2013.01); *G06T 2207/10081* (2013.01)

(56) References Cited

U.S. PATENT DOCUMENTS

| | | | | |
|---|---|---|---|---|
| 2011/0182492 | A1* | 7/2011 | Grass | A61B 6/5247 378/150 |
| 2016/0048965 | A1* | 2/2016 | Stehle | G06T 7/74 382/131 |
| 2017/0228900 | A1* | 8/2017 | Okabe | G06F 17/18 |
| 2019/0051412 | A1* | 2/2019 | Kano | G16H 10/60 |

FOREIGN PATENT DOCUMENTS

| | | |
|---|---|---|
| JP | 2014103065 | 6/2014 |
| JP | 2014236957 | 12/2014 |
| JP | 2016514533 | 5/2016 |
| WO | 2017199245 | 11/2017 |

OTHER PUBLICATIONS

"International Search Report (Form PCT/ISA/210)" of PCT/JP2018/047651, dated Mar. 19, 2019, with English translation thereof, pp. 1-5.
"Written Opinion of the International Searching Authority (Form PCT/ISA/237)" of PCT/JP2018/047651, dated Mar. 19, 2019, with English translation thereof, pp. 1-7.
"Office Action of Japan counterpart application," dated Jan. 19, 2021, with English translation thereof, pp. 1-6.

* cited by examiner

FIG. 5
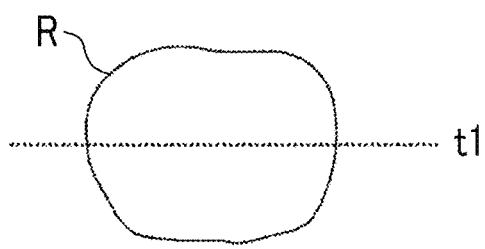
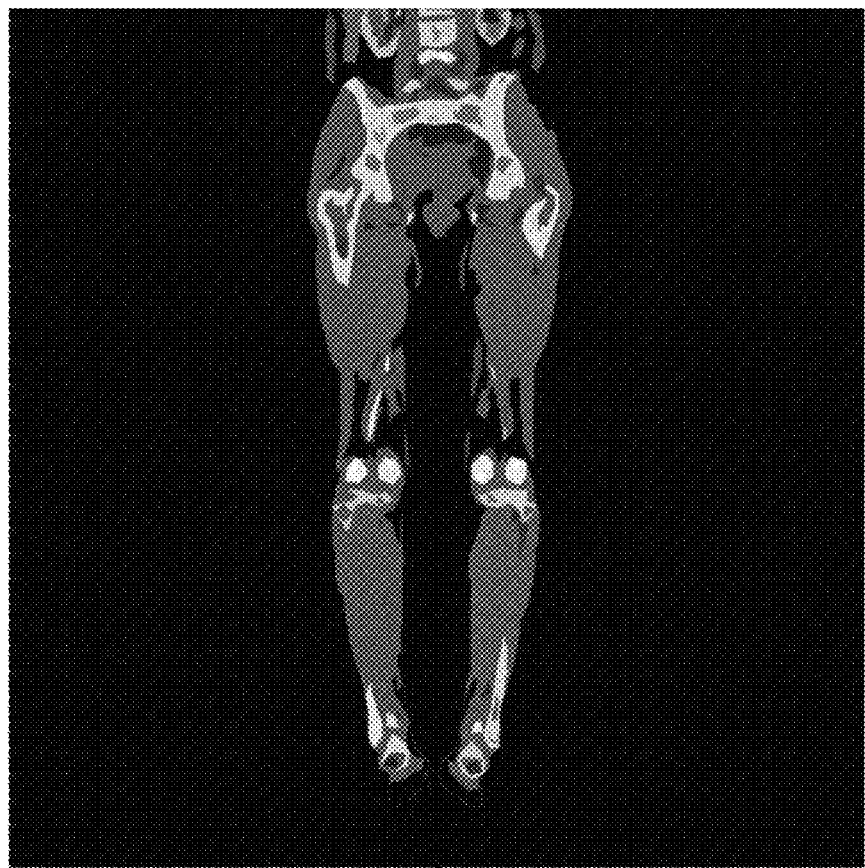

C1

C1

V

V

IMAGE PROCESSING APPARATUS, IMAGE PROCESSING METHOD, AND IMAGE PROCESSING PROGRAM

CROSS-REFERENCE TO RELATED APPLICATION

The present application is a continuation application of International Application No. PCT/JP2018/047651, filed Dec. 25, 2018, which claims priority to Japanese Patent Application No. 2018-043231, filed Mar. 9, 2018. The contents of these applications are incorporated herein by reference in their entirety.

BACKGROUND

Field of the Invention

The technology of the present disclosure relates to an image processing apparatus, an image processing method, and an image processing program.

Related Art

In recent years, as processing capability of a computer has improved, a three-dimensional display has come to be performed in various fields. With such a three-dimensional display, images of an object existing in a three-dimensional space viewed from various directions are displayed, whereby it is easy to grasp the object three-dimensionally.

However, in many cases, it takes time to perform a three-dimensional display, and in order to obtain an effect of rotating an object at hand, a method of preparing two-dimensional images viewed from various angles with respect to a certain object in advance and displaying the images by connecting them together may be used. In this method, a set of two-dimensional images viewed from different viewpoints is generated and distributed to a user, and the two-dimensional images are connected together and displayed using dedicated multimedia software.

On the other hand, in a medical field, in recent years, diagnosis is performed using volume data imaged by computed tomography (CT), magnetic resonance imaging (MRI), or the like. Although the volume data includes a large amount of information, it is difficult to grasp a position and a size of a lesion inside an organ even though a cross-sectional image is observed. Therefore, an anatomical structure such as an organ and a tissue using volume rendering is displayed three-dimensionally, whereby a position and a size of a lesion can be easily confirmed. In a case where such a structure is observed while being rotated, it is necessary to create images viewed from various directions by volume rendering each time the direction is changed.

Surface rendering can also be used as a method that enables three-dimensional grasp of a structure. In volume rendering, using a ray tracing method or the like, a projection image is generated by determining and adding coefficients according to pieces of information of all voxels on a line through which a line of sight extending from a viewpoint passes. Therefore, it takes time to display the projection image. On the other hand, in surface rendering, since a shape of an object is stored as a set of faces (polygons) that connect surfaces of a structure together, the amount of calculation is small and the object can be displayed at a relatively high speed.

Volume rendering or surface rendering is widely used in the medical field. For example, Japanese Re-Publication of PCT Application No. 2014-103065 discloses a method of performing display by using not only an image generated by volume rendering, but also two types of images of the volume rendering image and a surface rendering image generated by performing surface rendering on polygon data generated by converting volume data into surface information. First, a two-dimensional volume rendering image is generated by projecting volume data from a specific viewpoint, and a surface rendering image projected from the same viewpoint by using polygon data is composed on the two-dimensional volume rendering image and displayed on a display unit.

In volume rendering, only an organ or a tissue of an observation target is displayed or the organ around the tissue of the observation target translucent is made translucent, so that a positional relationship between the tissue and the organ of the observation target can be displayed in an easy-to-understand manner. However, since volume rendering uses pieces of information of all voxels on a line through which a line of sight passes, it takes time to perform calculation. Therefore, it takes time to perform calculation each time an image of the observation target viewed from different directions is generated, and display for performing observation while rotating the observation target may not be performed smoothly. On the other hand, in a case of surface data, since volume data is converted into surface information and projection is performed using the surface information, display can be performed at a certain speed, but fine texture information is lost.

On the other hand, in a case where a method of preparing two-dimensional images of the observation target viewed from various angles in advance and displaying the two-dimensional images by connecting them together is used, the observation target can be displayed while being rotated at a high speed without losing texture information. However, in order to display the target to be changed smoothly, it is necessary to prepare a considerably large number of two-dimensional images. In order to observe a certain structure in a removed state or in a displayed state, a two-dimensional image in a state where the structure is present and a two-dimensional image in a state where the structure is not present have to be prepared in advance, and an enormous number of two-dimensional images are required according to the number of combinations of structures.

SUMMARY

Therefore, in order to solve the above-described problems, an object of the technology of the present disclosure is to provide an image processing apparatus, an image processing method, and an image processing program capable of performing display while changing a viewpoint for observing an observation target at a high speed without preparing a large number of images in advance.

An image processing apparatus of the technology of the present disclosure comprises: a two-dimensional image acquisition unit that acquires a plurality of two-dimensional images generated from a three-dimensional image of a patient in a case where an observation target is viewed from a plurality of different viewpoints; a surface data acquisition unit that acquires surface data of each of a plurality of structures on the patient, the plurality of structures being extracted from the three-dimensional image; a composite image generation unit that generates a composite image in which a composite target image obtained by projecting the surface data of at least one of the plurality of structures on a screen of the two-dimensional image from a direction perpendicular to the screen and the two-dimensional image are composed; and a display switching control unit that receives an operation of displaying or non-displaying any of the plurality of structures and performs display by switching between the composite image of the composite target image and the two-dimensional image corresponding to the structure to be displayed and the two-dimensional image of the structure to be non-displayed according to the received operation.

An image processing method of the technology of the present disclosure performed by an image processing apparatus, comprises: acquiring a plurality of two-dimensional images generated from a three-dimensional image of a patient in a case where an observation target is viewed from a plurality of different viewpoints; acquiring surface data of each of a plurality of structures on the patient, the plurality of structures being extracted from the three-dimensional image; generating a composite image in which a composite target image obtained by projecting at least one piece of the surface data of the plurality of structures on a screen of the two-dimensional image from a direction perpendicular to the screen and the two-dimensional image are composed; and receiving an operation of displaying or non-displaying any of the plurality of structures and performing display by switching between the composite image of the composite target image and the two-dimensional image corresponding to the structure to be displayed and the two-dimensional image of the structure to be non-displayed according to the received operation.

An image processing program of the technology of the present disclosure causes a computer to execute: a two-dimensional image acquisition step of acquiring a plurality of two-dimensional images generated from a three-dimensional image of a patient in a case where an observation target is viewed from a plurality of different viewpoints; a surface data acquisition step of acquiring surface data of each of a plurality of structures on the patient, the plurality of structures being extracted from the three-dimensional image; a composite image generation step of generating a composite image in which a composite target image obtained by projecting at least one piece of the surface data of the plurality of structures on a screen of the two-dimensional image from a direction perpendicular to the screen and the two-dimensional image are composed; and a display switching control step of receiving an operation of displaying or non-displaying any of the plurality of structures and performing display by switching between the composite image of the composite target image and the two-dimensional image corresponding to the structure to be displayed and the two-dimensional image of the structure to be non-displayed according to the received operation.

The "composite image" refers to an image in which an image of a structure and a two-dimensional image are combined, and may be an image in which a part of the image is a structure and the remaining portion is the two-dimensional image, or may be an image in which the two images are combined so that one of the two images is made translucent and the other image is seen through by performing predetermined weighted-addition of pixel values of the two images.

It is desirable that the display switching control unit performs display by switching to a composite image which corresponds to a changed viewpoint and in which the two-dimensional image and the composite target image are composed in response to reception of an operation of changing the viewpoint for displaying the observation target.

The two-dimensional image may be an image obtained by removing the plurality of structures from the three-dimensional image, or may be an image including the plurality of structures in the three-dimensional image.

The two-dimensional image may have depth information in which the perpendicular direction is a depth direction, the surface data may have position information in the three-dimensional image, and the composite image generation unit may generate a composite image in which the composite target image is superimposed on the two-dimensional image for an image portion where a position of the surface data in the depth direction indicated by the depth information is in front of a position of the two-dimensional image indicated by the position information and the two-dimensional image is superimposed on the composite target image for an image portion where a position of the two-dimensional image in the depth direction is in front of the position of the surface data.

The composite image generation unit may generate the composite image by using a pixel value obtained by weighted-adding each pixel value of the two-dimensional image and a pixel value of a pixel of the composite target image corresponding to each pixel value of the two-dimensional image.

The two-dimensional image may be a two-dimensional projection image generated by projecting the three-dimensional image from a different viewpoint or a two-dimensional cross-sectional image in a different cross-sectional direction generated from the three-dimensional image.

The two-dimensional projection image may be a volume rendering image, a maximum intensity projection (MIP) image, a minimum intensity projection (MinIP) image, or a ray sum image.

The structure may be at least one of an organ, a bone, or a blood vessel.

Another image processing apparatus of the technology of the present disclosure comprises: a memory that stores instructions executed by a computer; and a processor configured to the stored instructions, in which the processor executes processing of: acquiring a two-dimensional image generated from a three-dimensional image of a patient; acquiring surface data of each of a plurality of structures on the patient, the plurality of structures being extracted from the three-dimensional image, generating a composite image in which a composite target image obtained by projecting at least one piece of the surface data of the plurality of structures on a screen of the two-dimensional image from a direction perpendicular to the screen and the two-dimensional image are composed, and receiving an operation of displaying or non-displaying any of the plurality of structures and performing display by switching between the composite image of the composite target image and the two-dimensional image corresponding to the structure to be displayed and the two-dimensional image of the structure to be non-displayed according to the received operation.

According to the technology of the present disclosure, it is possible to perform display while changing a viewpoint for observing an observation target at a high speed without preparing a large number of images in advance.

BRIEF DESCRIPTION OF THE DRAWINGS

FIG. 5 is a diagram showing an example of a relationship between a first cross-sectional image and a cross-sectional direction.

DETAILED DESCRIPTION

Figure 1:
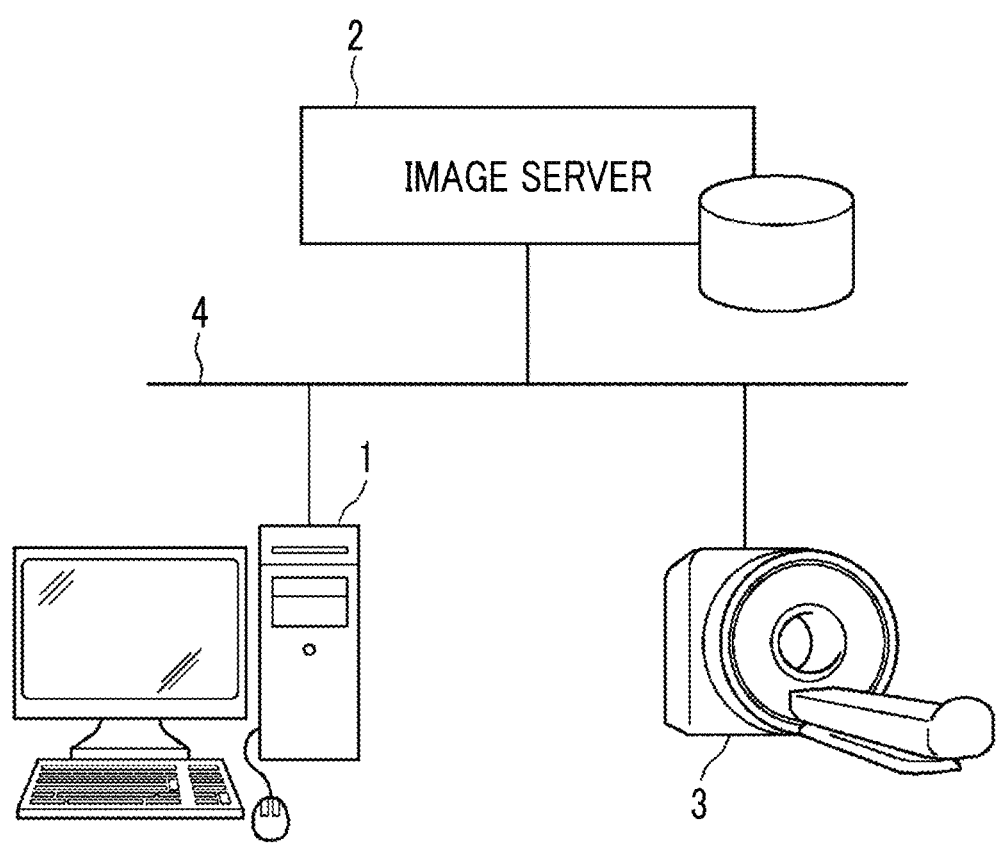
FIG. 1 is a diagram showing an example of a schematic configuration of a medical information system.

Hereinafter, a medical information system comprising an image processing apparatus according to an embodiment of the technology of the present disclosure will be described with reference to the drawings. FIG. 1 is a block diagram showing a schematic configuration of the medical information system according to the present embodiment.

In the medical information system according to the present embodiment, specifically, as shown in FIG. 1, an image processing apparatus 1, an image server 2, and an imaging device 3 (hereinafter, referred to as a modality) are connected to one another via a network 4 in a communicable state.

The modality 3 is, for example, a computed tomography (CT) device, a magnetic resonance imaging (MRI) device, an ultrasonic imaging device, or the like, and a captured three-dimensional image (hereinafter, referred to as volume data) is transmitted to and stored in the image server 2 via the network 4 according to a storage format and a communication standard in conformity with a digital imaging and communication in medicine (DICOM) standard.

The image processing apparatus 1 is a general-purpose computer, comprises a known hardware configuration such as a central processing unit (CPU) 10, a memory (main storage device), a storage (auxiliary storage device), an input/output interface, a communication interface, an input device, a display device, and a data bus, and a known operation system or the like is installed therein. The display device has a display or the like, and the input device has a keyboard and/or a pointing device such as a mouse. The storage is configured by a hard disk, a solid state drive (SSD), or the like. A graphics processing unit (GPU) may be provided in a computer as necessary. By installing an image processing program according to the present embodiment in the computer, the computer functions as the image processing apparatus 1. The image processing apparatus 1 has a function of requesting transmission of an image to the image server 2 and receiving an image from the image server 2, and is performed by executing a software program for each function.

The image processing program is distributed by being recorded in a recording medium such as a digital versatile disc (DVD) and a compact disc read only memory (CD-ROM), and is installed in a computer from the recording medium. Alternatively, the image processing program may be stored in a storage device of a server computer connected to a network or a network storage in a state accessible from the outside, and may be downloaded to a computer in response to a request from the outside and then installed.

Figure 2:
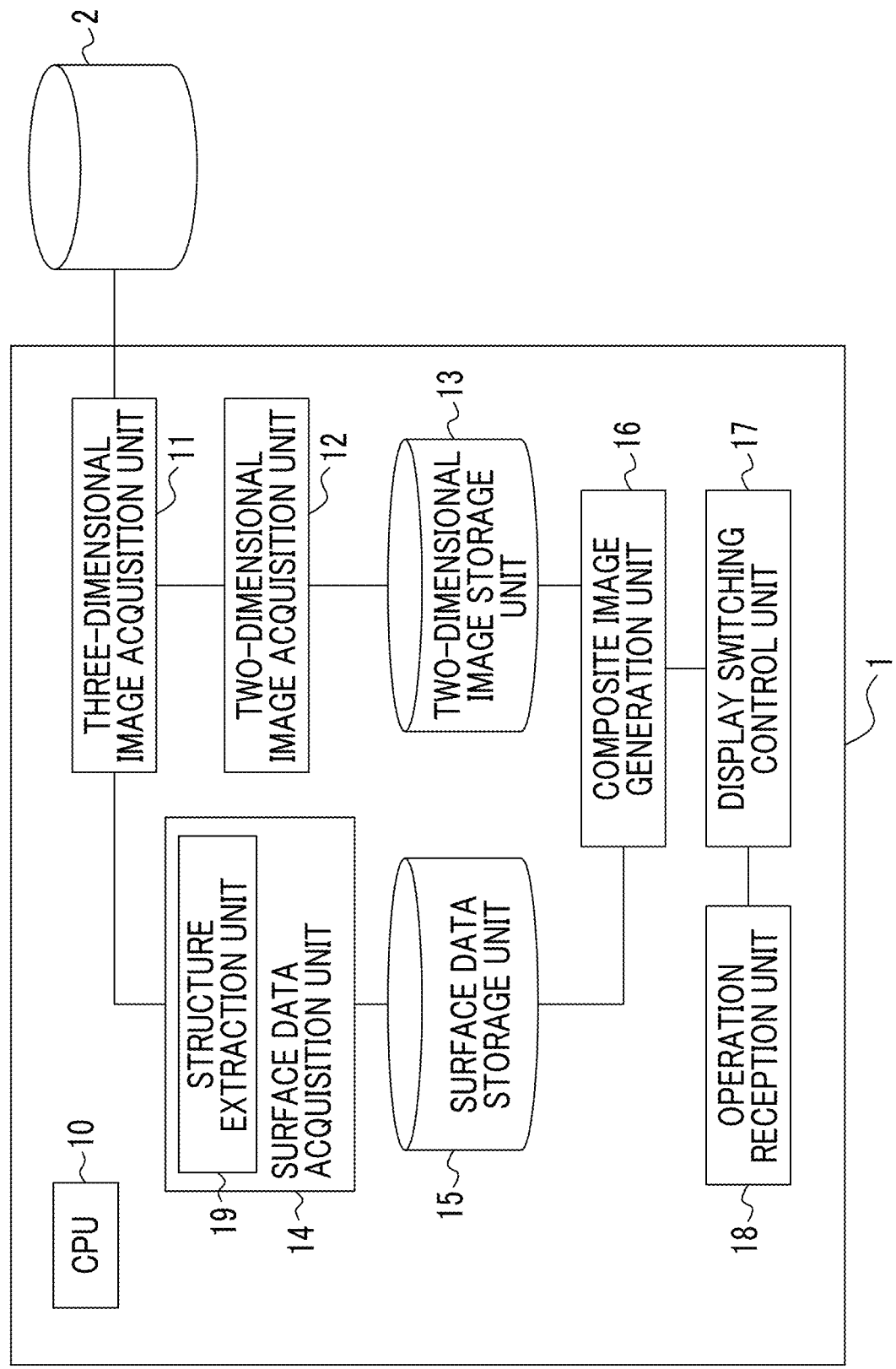
FIG. 2 is a schematic configuration diagram showing an example of an image processing apparatus according to the present embodiment.

In a case where the image processing apparatus 1 is activated, the image processing program is loaded on the memory and then executed by the CPU 10. Thus, as shown in FIG. 2, the image processing apparatus 1 functions as a three-dimensional image acquisition unit 11, a two-dimensional image acquisition unit 12, a two-dimensional image storage unit 13, a surface data acquisition unit 14, a surface data storage unit 15, a composite image generation unit 16, a display switching control unit 17, and an operation reception unit 18.

The three-dimensional image acquisition unit 11 acquires volume data of a patient, which has been imaged in advance. In the present embodiment, the volume data is data imaged by a CT device, an MRI device, an ultrasonic imaging device, or the like.

The volume data is stored in advance in the image server 2 together with identification information ID of a patient, and the three-dimensional image acquisition unit 11 reads out the volume data having the identification information ID of the patient from the image server 2 based on the identification information ID of the patient input by a user using an input device such as a keyboard and stores the volume data in a storage (not shown).

The two-dimensional image acquisition unit 12 acquires, from the volume data, a plurality of two-dimensional images in a case where an observation target is viewed from a plurality of different viewpoints. For example, in a case where an observation target is observed while being rotated, the observation target is observed while changing the viewpoint. An image in a case where the observation target is viewed from a plurality of the changed viewpoints is acquired as a two-dimensional image. Specifically, a two-dimensional projection image (hereinafter, simply referred to as a projection image) obtained by projecting volume data on a plane orthogonal to a line of sight that connects a gaze point (that is, the center of rotation) that is the center of interest of the observation target and a viewpoint in a case where the observation target is observed to each other, or a two-dimensional cross-sectional image (hereinafter, simply referred to as a cross-sectional image) that is parallel to a plane orthogonal to a line of sight can be used as a two-dimensional image. The projection image is, for example, a volume rendering image, a MIP image, a MinIP image, or a ray sum image. In addition, examples of the cross-sectional image include an axial cross-sectional (body axis cross-sectional) image, a sagittal cross-sectional image, a coronal cross-sectional image, and an oblique cross-sectional image.

The two-dimensional image acquisition unit 12 pre-generates the same number of two-dimensional images as the number of viewpoints and stores the images in the two-dimensional image storage unit 13. Alternatively, in a case where two-dimensional images of different types are prepared, the same number of two-dimensional images as the number of viewpoints is generated for each of the two-dimensional images of different types and stored in the two-dimensional image storage unit 13. For example, in a case where two types of two-dimensional images of a MIP image and a volume rendering image are prepared in advance, two-dimensional images having twice the number of viewpoints are generated and stored in the two-dimensional image storage unit 13. In order to smoothly perform rotation and display, it is desirable to prepare a plurality of the two-dimensional images with changed viewpoints, for example, 200 to 300. It is desirable that the number of two-dimensional images with changed viewpoints is changed according to the performance of hardware.

The two-dimensional image has depth information in which a direction perpendicular to a screen for displaying the two-dimensional image is a depth direction. In a case where the two-dimensional image is a projection image, for example, information on a distance between a position of a pixel of the volume data projected on the two-dimensional image and the screen of the two-dimensional image may be stored as depth information for each pixel of the two-dimensional image, but a position of a pixel of the volume data projected on each pixel of the two-dimensional image may be stored as depth information for each pixel of the two-dimensional image.

For example, as the depth information of the volume rendering image, a distance to a position where an opacity of a pixel on a line of sight as viewed from a viewpoint side exceeds a threshold value for the first time is stored as depth information for each pixel. For a transparent area where an opacity is lower than the threshold value (that is, a transparent or translucent area), the distance is a distance to a point at the end of an opaque structure located in a deep site (that is, an area where an opacity is equal to or higher than the threshold value). On the other hand, in a case where there is no object having an opacity equal to or higher than the threshold value in a certain pixel, the depth information is infinity. Infinity actually stores a maximum value of the distance. In addition, for example, since the MIP image projects a pixel value of a pixel having the highest density value on a line of sight that passes through the volume data, the depth information of the pixel of the volume data projected on the two-dimensional image is stored for each projected pixel. In addition, for example, since the MinIP image projects a pixel value of a pixel having the lowest density value on a line of sight that passes through the volume data, the depth information of the pixel of the volume data projected on the two-dimensional image is stored for each projected pixel. Furthermore, for example, since the ray sum image is an image obtained by simply adding pixel values, a distance to a center of the image that exists on a line of sight uniformly (that is, a range in which pixels having pixel values equal to or higher than the threshold value exist) is stored as depth information for each pixel.

In a case where the two-dimensional image is a cross-sectional image, a distance between a position of a pixel of a cross section of the volume data corresponding to each pixel of the two-dimensional image and the screen of the two-dimensional image may be stored as depth information for each pixel, and a position of a pixel of a cross section of the volume data corresponding to each pixel of the two-dimensional image may be stored as depth information for each pixel.

The volume data includes a structure of interest. A two-dimensional image may be generated from data in which the structure of interest remains in the volume data, but in a case where a tissue around the structure is observed, it is easier to observe the tissue without the structure. For example, in a case where volume rendering is used to generate a two-dimensional image, the volume rendering image is acquired by using data obtained by removing the structure from the volume data, so that an image in which the tissue around the structure can be easily confirmed can be generated.

The surface data acquisition unit 14 has a structure extraction unit 19 and acquires surface data of each of a plurality of structures extracted from a three-dimensional image and stores the surface data in the surface data storage unit 15. The surface data is a set of position information on a surface of the structure, and can be represented as a set of triangular meshes, for example.

The two-dimensional image storage unit 13 and the surface data storage unit 15 may be provided in the storage, but the image server 2 may be provided with the two-dimensional image storage unit 13 and the surface data storage unit 15 to receive the two-dimensional image and the surface data from the image server 2 as necessary.

The structure extraction unit 19 extracts an organ such as a heart, a kidney, a liver, a stomach, or an intestine, or a tissue such as a bone, a blood vessel, or a lymph gland. Extraction of an organ or a tissue can be performed using a known method such as a neural network that has undergone deep learning.

Figure 3:
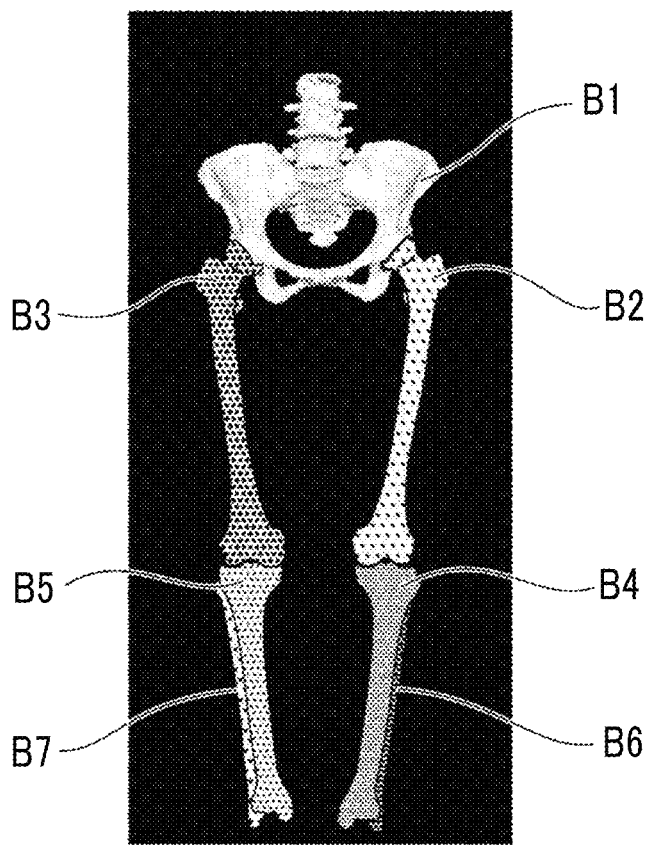
FIG. 3 is a diagram showing an example of a plurality of structures.
Figure 4:
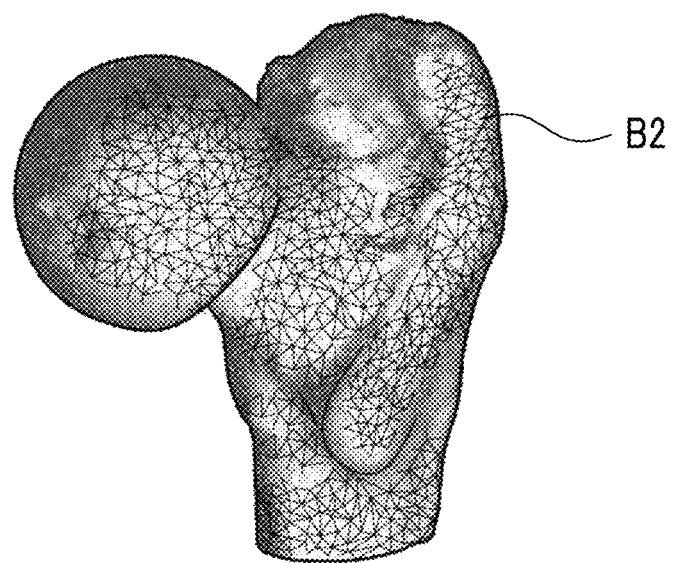
FIG. 4 is a diagram showing an example of surface data.

As an example, extraction of a structure and generation of surface data will be described for a case where the structure is a bone, with a lower body of a human body as an observation target. First, the surface data acquisition unit 14 extracts a hipbone and a sacrum B1, left and right femurs B2 and B3, left and right tibias B4 and B5, and left and right fibulas B6 and B7 by using the structure extraction unit 19 as shown in FIG. 3, and then generates surface data representing a surface shape of each bone. FIG. 4 shows an example of surface data in which an upper part of the left femur is represented by a set of triangular patches. Similarly, surface data in which a surface shape of each of the other bones is represented by a set of triangular patches is generated.

The composite image generation unit 16 takes out, from the two-dimensional image storage unit 13, a two-dimensional image in a case where the observation target is viewed from a specific viewpoint and generates a composite target image obtained by projecting the surface data of at least one of the plurality of structures on the screen in a direction perpendicular to the screen of the two-dimensional image (that is, in a normal direction), that is, a direction from the viewpoint of the two-dimensional image to the gaze point, and further generates a composite image in which the composite target image and the two-dimensional image are composed.

Figure 6:
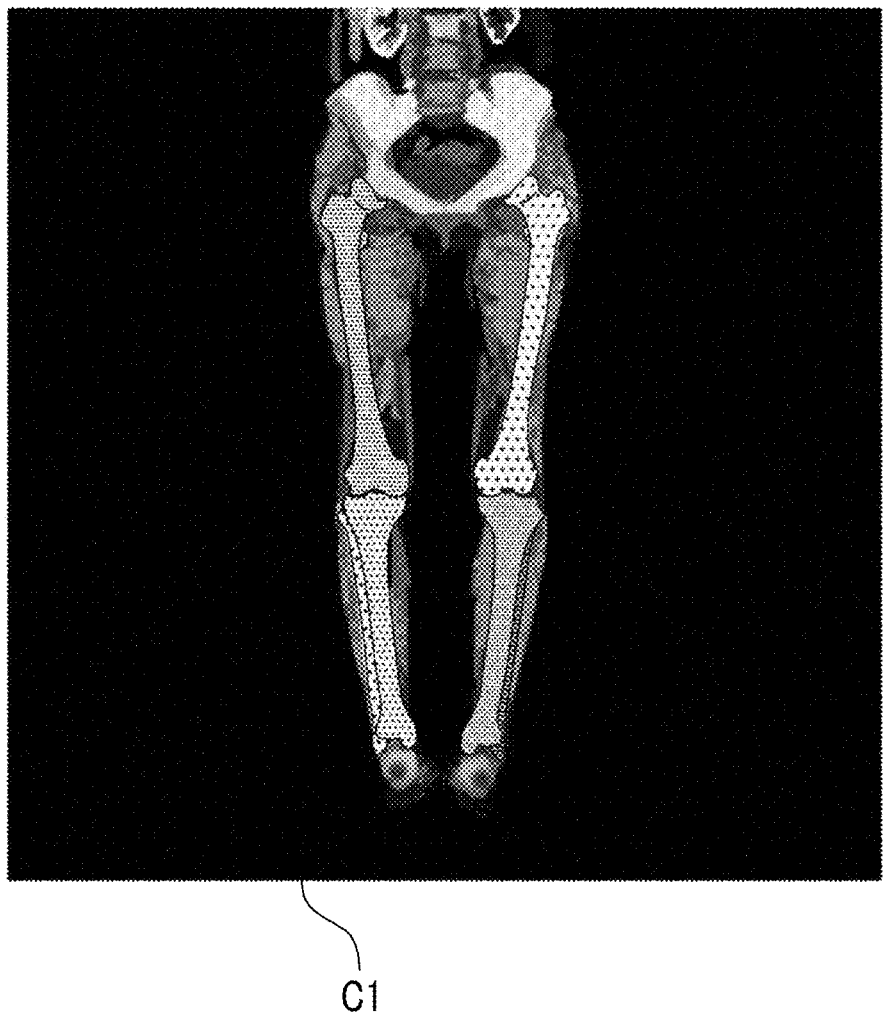
FIG. 6 is a diagram showing an example of a composite image in which structures are superimposed on the first cross-sectional image.
Figure 7:
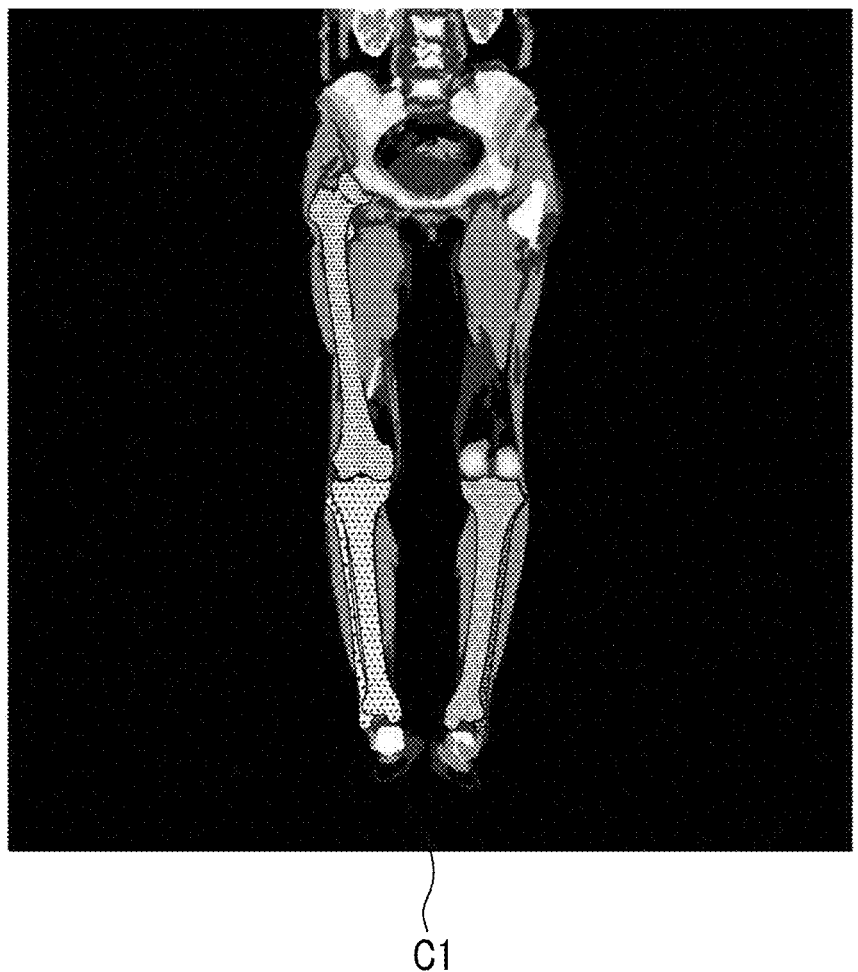
FIG. 7 is a diagram showing an example in which one of the structures superimposed on the first cross-sectional image is non-displayed.

FIG. 5 shows an example of a coronal cross-sectional image C1 of a lower body. An upper part of FIG. 5 shows a contour R of an abdomen cut by a plane perpendicular to a body axis. The coronal cross-sectional image C is an image obtained by cutting the abdomen in a direction of t1. FIG. 6 shows an example of a composite image in which a composite target image is generated by projecting surface data of the bones B1, B2, B3, B4, B5, B6, and B7 in a direction perpendicular to the coronal cross-sectional image C1 and the composite target image and the coronal cross-sectional image C1 are composed. In FIG. 7, since the bone B2 is non-displayed, the coronal cross-sectional image C1 is displayed on a portion of the bone B2, and the composite images are displayed on portions of the bones B1, B3, B4, B5, B6, and B7 to be displayed.

Figure 8:
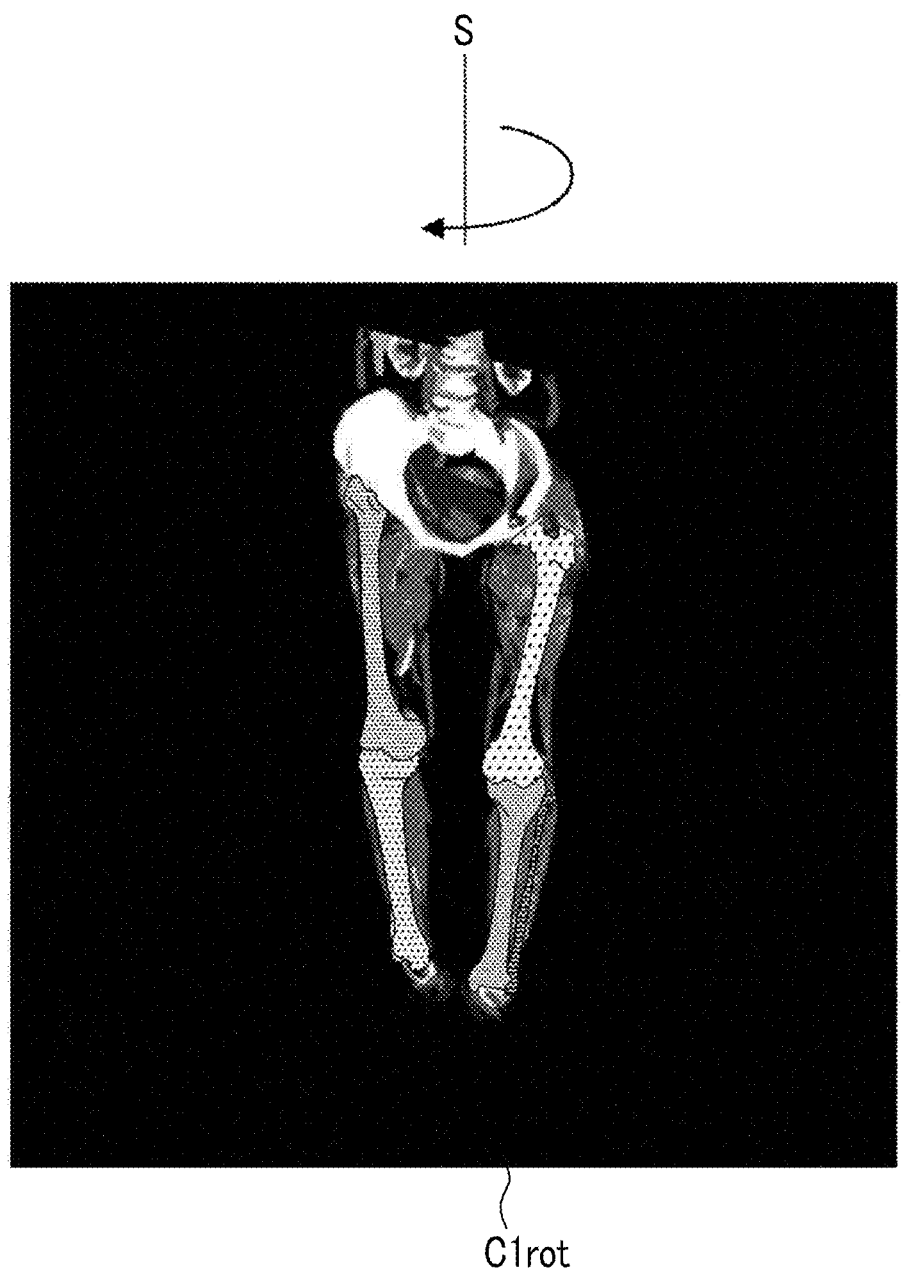
FIG. 8 is a diagram showing an example of a composite image in which the structures are superimposed on the first cross-sectional image in a case where the cross-sectional image is rotated.

The composite image generation unit 16 generates a composite image in which the composite target image is superimposed on the two-dimensional image for an image portion where a position of the surface data in the depth direction is in front of a position of the two-dimensional image indicated by the depth information and the two-dimensional image is superimposed on the composite target image for an image portion where a position of the two-dimensional image in the depth direction is in front of the position of the surface data. For example, a position of the coronal cross-sectional image C1 indicated by information in the depth direction is compared with a position of the surface data of the bones B1, B3, B4, B5, B6, and B7 indicated by the position information, and as a result, the image in front of the screen is displayed. In the example of FIG. 6, the position of the coronal cross-sectional image C1 exists in front of the sacrum of the bone B1 and behind the hipbone of the bone B1, so that the sacrum is not displayed in a composite image of a waist portion, but the hipbone is displayed therein. Specifically, for example, the structure in the front may be displayed using a Z-buffer method. Furthermore, FIG. 8 is an example in which the coronal cross-sectional image C1 is displayed by being rotated around a body axis.

Figure 9:
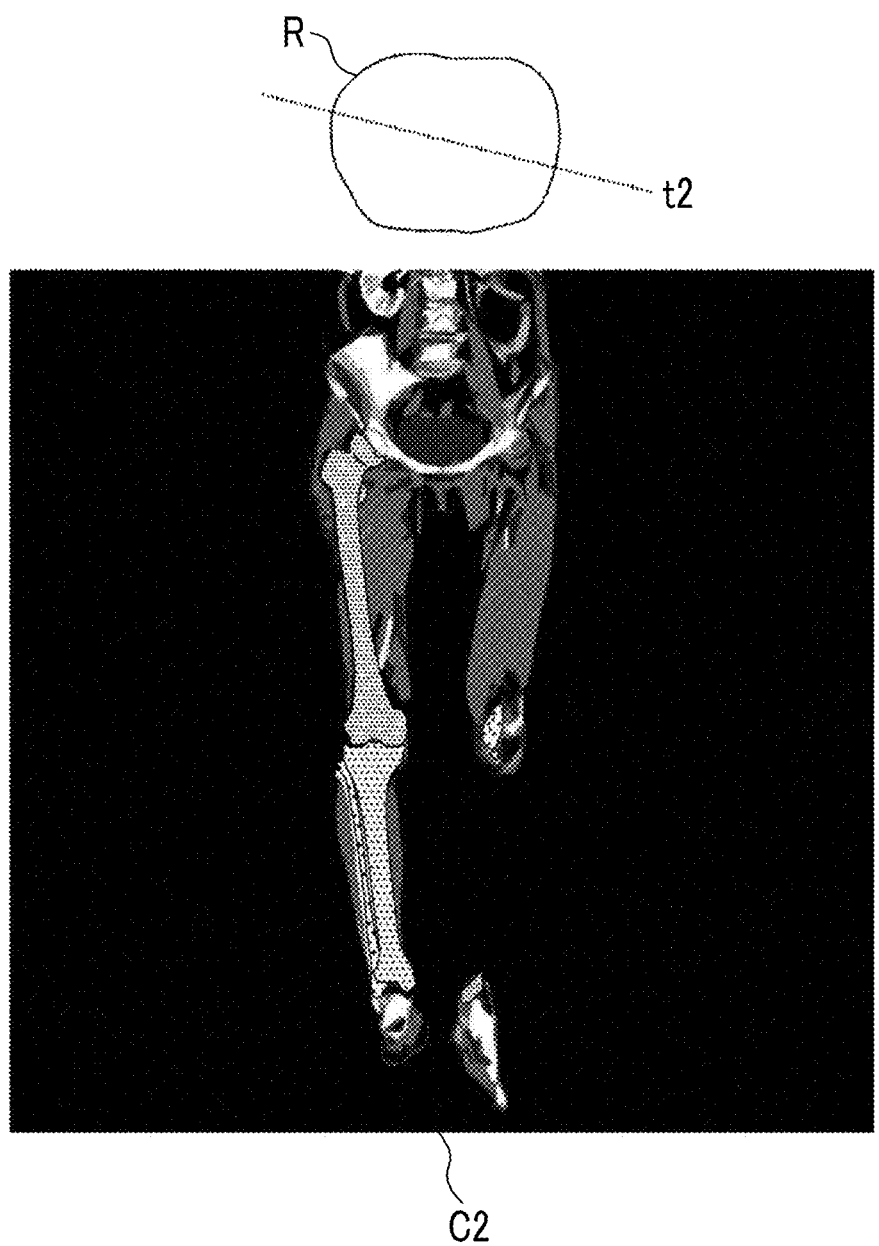
FIG. 9 is a diagram showing an example of a relationship between a second cross-sectional image and a cross-sectional direction.
Figure 10:
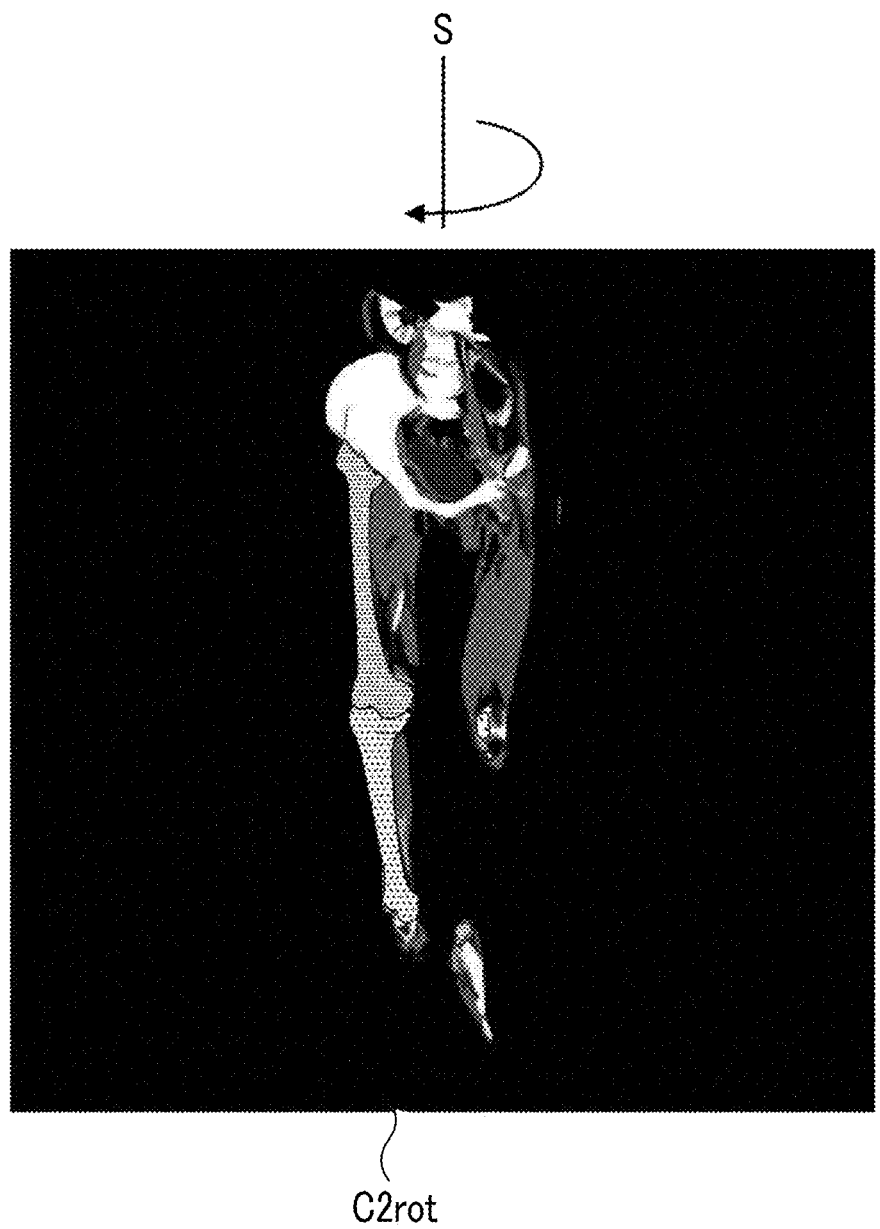
FIG. 10 is a diagram showing an example of a composite image in which the structures are superimposed on the second cross-sectional image in a case where the cross-sectional image is rotated.

FIG. 9 is an example of a composite image in which an oblique cross-sectional image C2 in a case where a cross-sectional direction is t2 and the composite target image obtained by projecting the surface data of the bones B1, B2, B3, B4, B5, B6, and B7 are composed. The cross-sectional direction t2 is tilted from the cross-sectional direction t1 of the coronal cross-sectional image C1. Therefore, the positions of the bones B2, B4, and B6 exist behind the oblique cross-sectional image C2, so that the bones B2, B4, and B6 are not displayed. In addition, a part of the hipbone B1 on a right side of the oblique cross-sectional image C2 in FIG. 9 also exists behind the oblique cross-sectional image C2 and thus is not displayed. FIG. 10 is an example in which the oblique cross-sectional image C2 is displayed by being rotated around a body axis S.

Figure 11:
FIG. 11 is a diagram showing an example of volume rendering.
Figure 12:
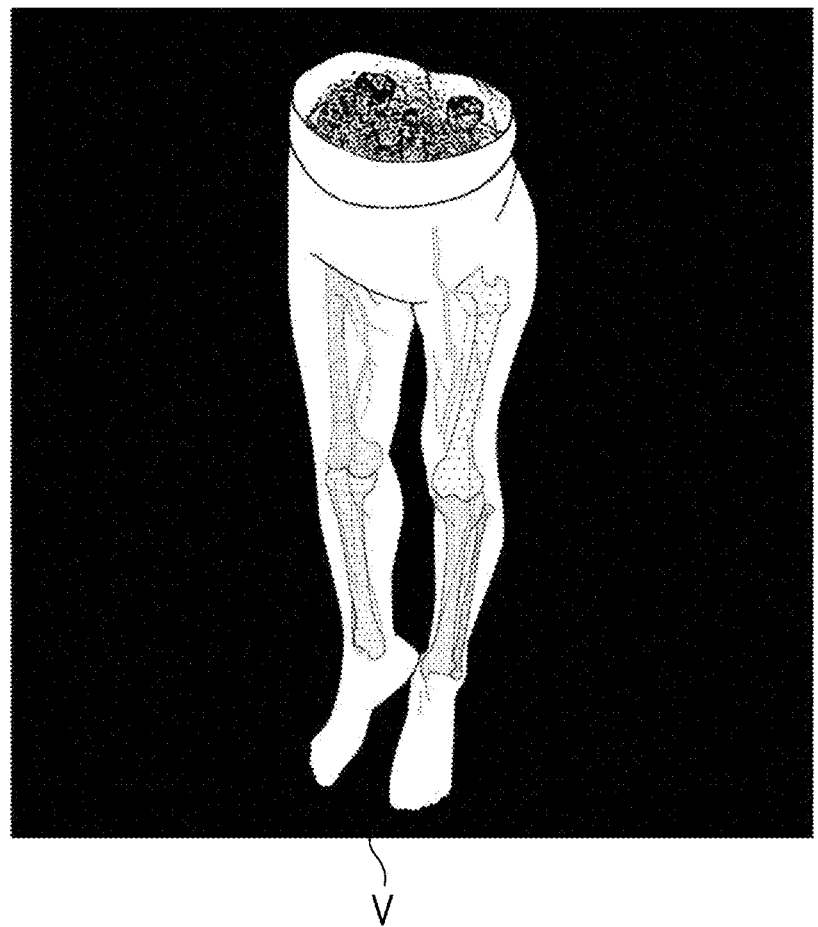
FIG. 12 is a diagram showing an example of a composite image in which structures are superimposed on volume rendering.
Figure 13:
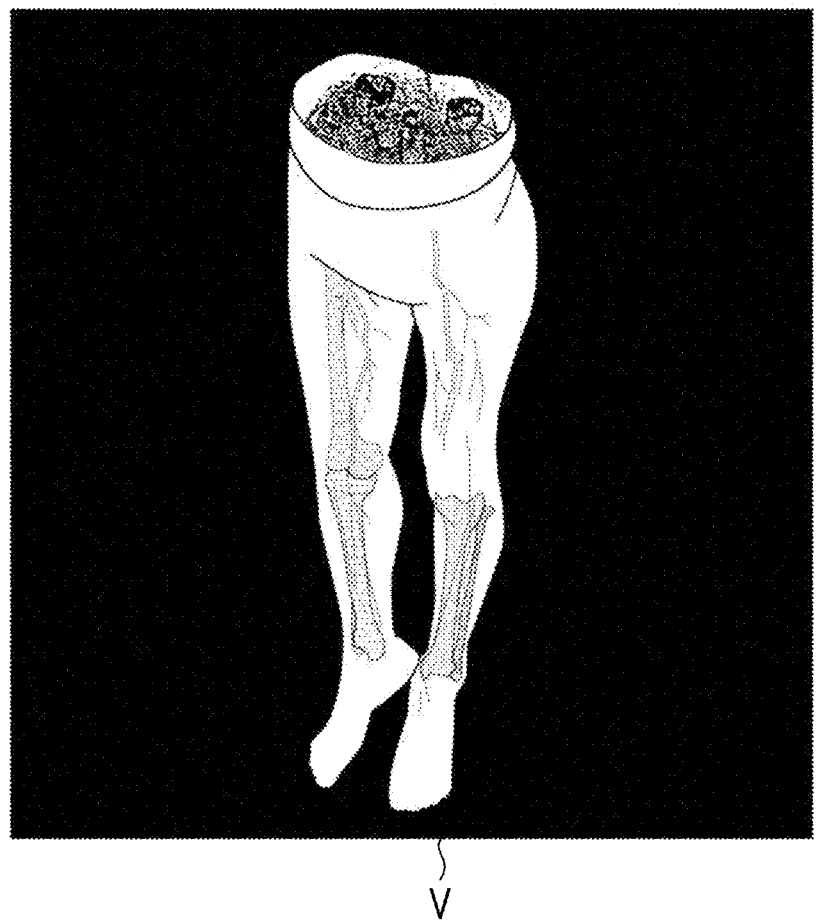
FIG. 13 is a diagram showing an example in which one of the structures superimposed on volume rendering is non-displayed.

Alternatively, the composite image generation unit 16 may generate the composite image by using a pixel value obtained by weighted-adding each pixel value of the two-dimensional image and a pixel value of a pixel of the composite target image corresponding to each pixel value of the two-dimensional image. FIG. 11 shows an example of a volume rendering image V created using data obtained by removing bones from volume data. FIG. 12 shows an example of a composite image generated by performing weighted-addition of pixel values of the composite target image obtained by projecting the surface data of the bones B1, B2, B3, B4, B5, B6, and B7 and pixel values of the volume data. By changing a weight of the weighted-addition in this way, it is possible to generate an image in which leg muscles are translucent and bones can be observed. FIG. 13 shows an example in which the bone B2 of FIG. 12 is non-displayed.

Whether the composite image generation unit 16 generates a composite image by comparing positions of the two-dimensional image and the composite target image, or generates a composite image by using a pixel value obtained by weighted-adding each pixel value of the two-dimensional image and a pixel value of a pixel of the composite target image corresponding to each pixel value of the two-dimensional image is determined according to a preset parameter. Alternatively, a user may perform an operation of changing the parameter to switch what kind of composite image is generated.

The operation reception unit 18 receives an operation of changing a position of a viewpoint, an operation of selecting one of a plurality of structures, or an operation of displaying or non-displaying the structure, which is performed using an input device such as a keyboard or a mouse. For example, an operation of rotating a trackball provided on a mouse or an operation of drawing a predetermined locus on a screen using the mouse may be the operation of changing the position of the viewpoint. Alternatively, for example, an operation of pointing a displayed structure with a mouse or the like or an operation of displaying a name of the structure on a screen to select the name may be the operation of selecting the structure. In addition, for example, an operation of pressing a button (for example, a delete key and an insert key) on a predetermined keyboard while selecting the structure may be the operation of switching between non-display and display.

In a case where the operation of changing the position of the viewpoint is received, the display switching control unit 17 performs display by switching from a currently displayed composite image to a composite image of a two-dimensional image and a composite target image corresponding to the changed viewpoint. As the composite image, each time the viewpoint is changed, a composite image corresponding to the changed viewpoint is generated by the composite image generation unit 16.

The operation of displaying or non-displaying the structure is received, the display switching control unit 17 performs display by switching the display such that the composite image generated by the composite image generation unit 16 using the surface data and the two-dimensional image is displayed on a portion corresponding to the structure to be displayed, and the two-dimensional image is displayed on a portion of the structure to be non-displayed. That is, the image portion corresponding to the structure to be displayed is an image in which the structure is shown by displaying the composite image of the composite target image of the structure and the two-dimensional image, and the image portion corresponding to the structure to be non-displayed is an image in which the structure is removed by displaying the two-dimensional image.

Figure 14:
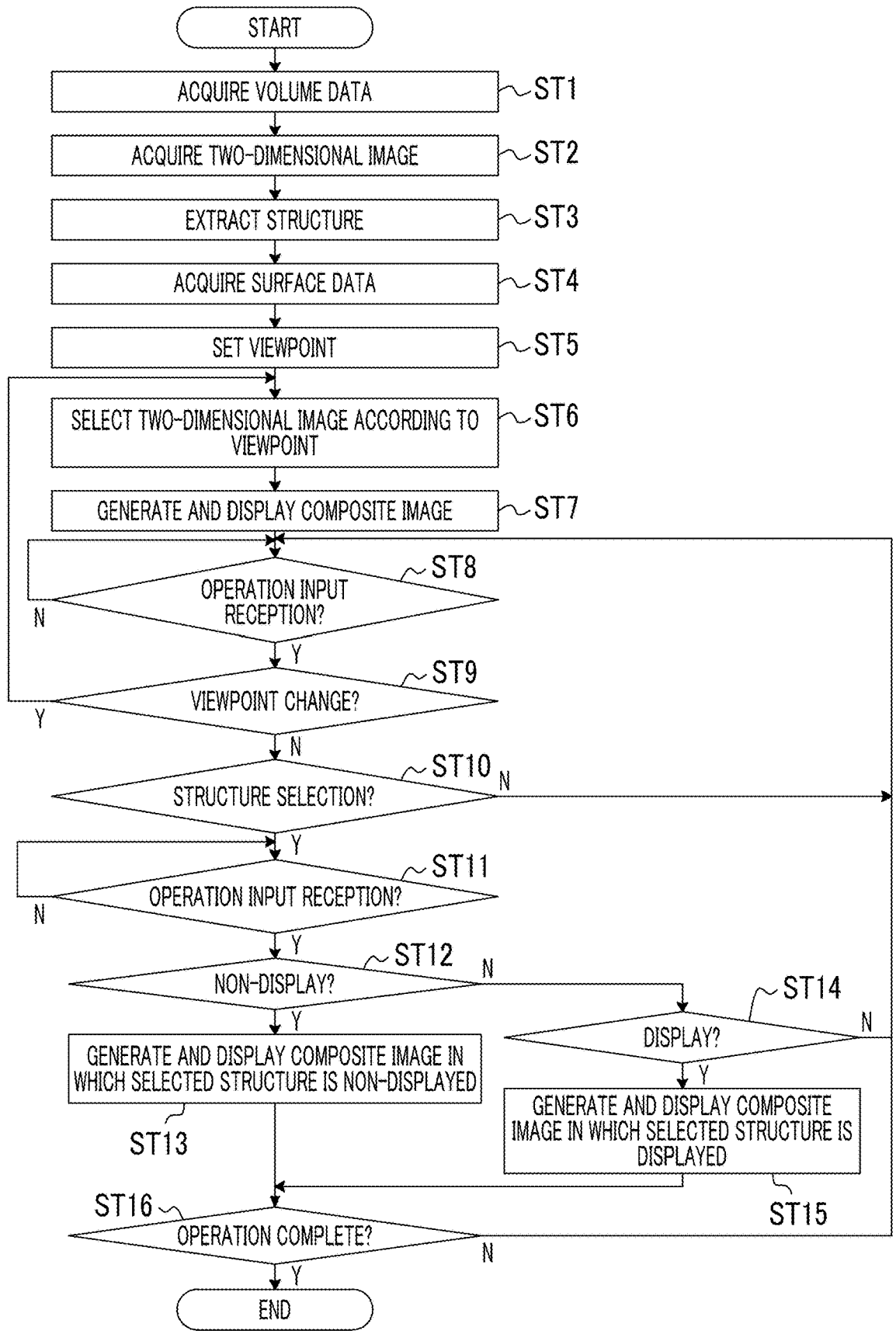
FIG. 14 is a flowchart illustrating an example of a processing flow of the image processing apparatus.

Next, a processing flow of the image processing apparatus will be described with reference to a flowchart of FIG. 14. In the present embodiment, a case where a bone is switched between display and non-display, with a lower body as an observation target will be described as an example.

First, in a case where a user inputs an ID that is identification information of a patient, the three-dimensional image acquisition unit 11 transmits the patient ID to the image server 2, acquires volume data of the patient corresponding to the ID from the image server 2, and temporarily stores the volume data in a storage (step ST1). Next, the two-dimensional image acquisition unit 12 generates a cross-sectional image in a case where the observation target is viewed from a plurality of viewpoints from the volume data and stores the cross-sectional image in the two-dimensional image storage unit 13 (step ST2). Furthermore, the surface data acquisition unit 14 extracts, for example, each of regions of the bones B1, B2, B3, B4, B5, B6, and B7 (see FIG. 3) from the volume data by using the structure extraction unit 19 (step ST3), and generates surface data representing a surface shape of each of these bone regions is generated and stores the surface data in the surface data storage unit 15 (step ST4).

First, an observation target in a case of being viewed from a predetermined viewpoint is displayed. For example, the viewpoint is set in front of a lower body (step ST5). The composite image generation unit 16 selects a cross-sectional image of the lower body as seen from the front, for example, the coronal cross-sectional image C1 shown in FIG. 5, from the two-dimensional image storage unit 13 (step ST6). Next, the surface data of each of the bones B1, B2, B3, B4, B5, B6, and B7 is taken out from the surface data storage unit 15, and a composite target image is generated by projecting each surface data on the coronal cross-sectional image C in a front direction. In this case, in a case where a position of the surface data in the depth direction exists in front of a position of each pixel of the cross-sectional image, the composite target image is superimposed on the coronal cross-sectional image C1. On the other hand, in a case where the position of each pixel of the coronal cross-sectional image C1 in the depth direction exists in front of the position of the surface data, the coronal cross-sectional image C1 is superimposed on the composite target image and displayed on a display (step ST7).

Next, in a case where the operation reception unit 18 receives an operation input, determination in step ST8 is affirmed. Subsequently, it is determined whether or not the operation is an operation of changing the viewpoint. In a case where a user performs an operation for changing the viewpoint, determination in step ST9 is affirmed and the processing returns to step ST6. The composite image generation unit 16 selects a cross-sectional image according to the changed viewpoint (step ST6), and generate a composite target image by projecting the surface data of each of the bones B1, B2, B3, B4, B5, B6, and B7 on the cross-sectional image from the changed viewpoint and further generates a composite image which corresponds to the changed viewpoint and in which the cross-sectional image and the composite target image are composed. The display switching control unit 17 performs display by switching from a currently displayed composite image to a newly generated composite image (step ST7). Subsequently, in a case where an operation for changing the viewpoint is performed, determinations in step ST8 and step ST9 are affirmed as described above, and the processing returns to step ST6. Again, the composite image generation unit 16 generates a composite image corresponding to the changed viewpoint, and the display switching control unit 17 performs display by switching from a currently displayed composite image to a newly generated composite image. While the user performs the operation of changing the viewpoint, the processing items of steps ST6 to ST9 are repeated, and display is performed by switching from the viewpoint according to the operation to the composite image displaying the observation target.

Next, a case where a structure is non-displayed will be described. In a case where the operation reception unit 18 receives an operation of selecting the displayed bone B2 (see FIG. 6) using a mouse or the like by the user, step ST8 is affirmed. Since the received operation is an operation of selecting the structure, determination in step ST9 is negated and determination in step ST10 is affirmed. Following the selection of the structure, the operation reception unit 18 waits for next operation input (step ST11). In a case where the user performs an operation of non-displaying the bone B2, determination in step ST12 is affirmed, and the composite image generation unit 16 generates a composite image in which the cross-sectional image and a composite target image obtained by projecting the surface data of the bones B1, B3, B4, B5, B6, and B7 excluding the bone B2 to be non-displayed are composed. Furthermore, in a case where the display switching control unit 17 performs display by switching a currently displayed composite image to a newly generated composite image (step ST13), the image in which the bone B2 is non-displayed is displayed on the display. Determination in step ST16 is negated and the processing returns to step ST8 until all operations are completed.

Next, a case where a structure is switched from non-display to display will be described. For example, in a case where the operation reception unit 18 receives an operation of selecting the bone B2 from structures in a non-display list by the user, step ST8 is affirmed. Since the received operation is an operation of selecting the structure, determination in step ST9 is negated and determination in step ST10 is affirmed. Following the selection of the structure, the operation reception unit 18 waits for next operation input (step ST1). Subsequently, in a case where the user performs an operation of displaying the bone B2, determination in step ST12 is negated and determination in step ST14 is affirmed. The composite image generation unit 16 generates a composite image in which a composite target image obtained by projecting the surface data of the bones B1, B2, B3, B4, B5, B6, and B7 added with the bone B2 to be displayed and the cross-sectional image are composed. Furthermore, in a case where the display switching control unit 17 performs display by switching a currently displayed composite image to a newly generated composite image (step ST15), the image in which the bone B2 is displayed is displayed on the display. Determination in step ST16 is negated and the processing returns to step ST8 until all operations are completed.

As described in detail above, by creating a two-dimensional image in a case where an observation target is viewed from a plurality of viewpoints in advance and creating surface data of a structure of interest of which a display state is to be changed from an organ or a tissue, the display for rotating the observation target can be performed at a high speed, and the structure of interest can be display or non-displayed. In addition, by having only the structure of interest such as a bone as the surface data, it is not necessary to prepare all two-dimensional images in which the structure is displayed or non-displayed, and a storage capacity can be saved.

In the above description, the case is described in which the image processing apparatus performs all the processing items of acquiring the two-dimensional image, acquiring the surface data from the volume data, and generating and displaying the composite image in which the two-dimensional image and the composite target image obtained by projecting the surface data are composed while changing the viewpoint. However, the processing of acquiring the two-dimensional image and acquiring the surface data from the volume data, which is shown in ST1 to ST4 of FIG. 14, may be performed by a high-performance computer with a high arithmetic processing capability, such as an image processing server, and the processing of performing display while generating the composite image in which the two-dimensional image and the composite target image while changing the viewpoint, which is shown in ST5 to ST16 of FIG. 14, may be performed by a terminal different from the image processing server. As a terminal that generates and displays the composite image while changing the viewpoint, for example, a terminal for browsing having a relatively lower arithmetic processing performance than the image processing server, such as a smartphone, a tablet terminal, a head-mounted display, or a notebook personal computer (PC) may be used. In addition, in a case where the terminal device repeatedly displays the composite image while changing the viewpoint, the terminal is not necessarily required to be connected to the image processing server, and the terminal device receives and stores the two-dimensional image and the surface data from the image processing server in advance, so that it is possible to generate and display the composite image while changing the viewpoint even in an offline environment.

In the above embodiment, a hardware structure of a processing unit that executes various items of processing of the image processing apparatus is the following various processors. The various processors include a central processing unit (CPU) that is a general-purpose processor that executes software (programs) to function as various processing units, a programmable logic device (PLD) that is a processor capable of changing a circuit configuration after manufacture, such as a field programmable gate array (FPGA), and an exclusive electric circuit that is a processor having a circuit configuration exclusively designed to execute a specific process, such as an application specific integrated circuit (ASIC).

One processing unit may be constituted by one of these various processors, or may be constituted by a combination of two or more processors of the same type or different types (for example, a combination of a plurality of FPGAs or a combination of a CPU and an FPGA). In addition, a plurality of the processing units may be constituted by one processor. As an example in which the plurality of processing units are constituted by one processor, first, as represented by a computer such as a client or a server, one processor is constituted by a combination of one or more CPUs and software and this processor functions as the plurality of processing units. Second, as represented by a system on chip (SoC) or the like, a processor that realizes the functions of the entire system including the plurality of processing units by using one integrated circuit (IC) chip is used. As described above, the various processing units are constituted by using one or more of the above described various processors as a hardware structure.

What is claimed is:

1. An image processing apparatus comprising:
a processor configured to:
acquire a plurality of two-dimensional images generated from a three-dimensional image of a patient in a case where an observation target is viewed from a plurality of different viewpoints;
acquire surface data of each of a plurality of structures on the patient, the plurality of structures being extracted from the three-dimensional image;
generate a composite image in which a composite target image obtained by projecting the surface data of at least one of the plurality of structures on a screen of the two-dimensional image from a direction perpendicular to the screen and the two-dimensional image are composed;
receive an operation of non-displaying a structure to be non-displayed selected from the plurality of structures, generate and display a composite image in which a first composite target image obtained by projecting the surface data of the plurality of structures excluding the structure to be non-displayed on the screen of the two-dimensional image from the direction perpendicular to the screen and the two-dimensional image are composed according to the operation of non-displaying the structure to be non-displayed, and receive an operation of displaying a structure to be displayed which has been non-displayed and is selected from a non-displayed structure list, generate and display a composite image in which a second composite target image obtained by projecting the surface data of the plurality of structures added with the structure to be displayed on the screen of the two-dimensional image from the direction perpendicular to the screen and the two-dimensional image are composed according to the operation of displaying the structure to be displayed.

2. The image processing apparatus according to claim 1, wherein the processor is further configured to perform display by switching to a composite image which corresponds to a changed viewpoint and in which the two-dimensional image and the composite target image are composed in response to reception of an operation of changing the viewpoint for displaying the observation target.

3. The image processing apparatus according to claim 1, wherein the two-dimensional image is acquired from an image obtained by removing the plurality of structures from the three-dimensional image, or is acquired from an image including the plurality of structures in the three-dimensional image.

4. The image processing apparatus according to claim 1, wherein the two-dimensional image has depth information in which the perpendicular direction is a depth direction,
wherein the surface data has position information in the three-dimensional image, and
wherein the processor is further configured to generate a composite image in which the composite target image is superimposed on the two-dimensional image for an image portion where a position of the surface data in the depth direction indicated by the depth information is in front of a position of the two-dimensional image indicated by the position information and the two-dimensional image is superimposed on the composite target image for an image portion where a position of the two-dimensional image in the depth direction is in front of the position of the surface data.

5. The image processing apparatus according to claim 1, wherein the processor is further configured to generate the composite image by using a pixel value obtained by weighted-adding each pixel value of the two-dimensional image and a pixel value of a pixel of the composite target image corresponding to each pixel value of the two-dimensional image.

6. The image processing apparatus according to claim 1, wherein the two-dimensional image is a two-dimensional projection image generated by projecting the three-dimensional image from a different viewpoint or a two-dimensional cross-sectional image in a different cross-sectional direction generated from the three-dimensional image.

7. The image processing apparatus according to claim 6, wherein the two-dimensional projection image is a volume rendering image, a MIP image, a MinIP image, or a ray sum image.

8. The image processing apparatus according to claim 1, wherein the structure is at least one of an organ, a bone, or a blood vessel.

9. An image processing method performed by an image processing apparatus, the method comprising:
acquiring a plurality of two-dimensional images generated from a three-dimensional image of a patient in a case where an observation target is viewed from a plurality of different viewpoints;

acquiring surface data of each of a plurality of structures on the patient, the plurality of structures being extracted from the three-dimensional image;

generating a composite image in which a composite target image obtained by projecting the surface data of at least one of the plurality of structures on a screen of the two-dimensional image from a direction perpendicular to the screen and the two-dimensional image are composed;

receiving an operation of non-displaying a structure to be non-displayed selected from the plurality of structures, generating and displaying a composite image in which a first composite target image obtained by projecting the surface data of the plurality of structures excluding the structure to be non-displayed on the screen of the two-dimensional image from the direction perpendicular to the screen and the two-dimensional image are composed according to the operation of non-displaying the structure to be non-displayed, and receiving an operation of displaying a structure to be displayed which has been non-displayed and is selected from a non-displayed structure list, generating and displaying a composite image in which a second composite target image obtained by projecting the surface data of the plurality of structures added with the structure to be displayed on the screen of the two-dimensional image from the direction perpendicular to the screen and the two-dimensional image are composed according to the operation of displaying the structure to be displayed.

10. A non-transitory computer-readable recording medium storing therein an image processing program that cause a computer to:

acquire a plurality of two-dimensional images generated from a three-dimensional image of a patient in a case where an observation target is viewed from a plurality of different viewpoints;

acquire surface data of each of a plurality of structures on the patient, the plurality of structures being extracted from the three-dimensional image;

generate a composite image in which a composite target image obtained by projecting the surface data of at least one of the plurality of structures on a screen of the two-dimensional image from a direction perpendicular to the screen and the two-dimensional image are composed;

receive an operation of non-displaying a structure to be non-displayed selected from the plurality of structures, generate and display a composite image in which a first composite target image obtained by projecting the surface data of the plurality of structures excluding the structure to be non-displayed on the screen of the two-dimensional image from the direction perpendicular to the screen and the two-dimensional image are composed according to the operation of non-displaying the structure to be non-displayed, and receive an operation of displaying a structure to be displayed which has been non-displayed and is selected from a non-displayed structure list, generate and display a composite image in which a second composite target image obtained by projecting the surface data of the plurality of structures added with the structure to be displayed on the screen of the two-dimensional image from the direction perpendicular to the screen and the two-dimensional image are composed according to the operation of displaying the structure to be displayed.

\* \* \* \* \*